United States Patent [19]

Silver et al.

[11] Patent Number: 4,994,370

[45] Date of Patent: Feb. 19, 1991

[54] DNA AMPLIFICATION TECHNIQUE

[75] Inventors: Jonathan Silver; Vijaya R. Keerikatte, both of Bethesda, Md.

[73] Assignee: The United States of America as represented by the Department of Health and Human Services, Washington, D.C.

[21] Appl. No.: 292,814

[22] Filed: Jan. 3, 1989

[51] Int. Cl.$^5$ .................. C12Q 1/68; C12P 19/34; C12N 9/22; G01N 33/566

[52] U.S. Cl. ................................ 435/6; 435/91; 435/18; 435/199; 435/15; 435/193; 436/501; 436/94

[58] Field of Search .............. 435/6, 18, 19, 199, 435/91, 172.3; 935/77, 78; 436/501, 94

[56] References Cited

U.S. PATENT DOCUMENTS 4,693,979 9/1987 Stetter et al. ................ 435/199
4,800,159 1/1989 Mullis et al. ................ 435/172.3

OTHER PUBLICATIONS

Maniatis et al., Molecular Cloning, a Lab. Manual, Cold Spring Harbor Lab., 1982.
Davis, L. G et al., Basic Methods in Molecular Biology, Elsevier, N.Y., 1986. (contents pp.).
Davis, R. W. et al., A Manual for Genetic Engineering: Advanced Bact. Genetics, Cold Spring Harbor Lab., 1980 (contents pp.).
Ochman, H., et al., Genetics 120: 621-623 (Nov., 1988).
Triglia, T., et al., Nucleic Acids Research, 16, No. 16: 8186 (Aug. 1988).
Silver, J., et al., Cold Spring Harbor Laboratory Meeting on RNA Tumor Viruses, p. 9, May 1988.
Mullis, K. B., "The Polymerase Chain Reaction: Why It Works" in Current Communications in Molecular Biology (Cold Spring Harbor Laboratory Press, H. A. Erlich, Ed.), pp. 237-243, (1989).

Primary Examiner—Robert A. Wax
Assistant Examiner—Stephanie W. Zitomer
Attorney, Agent, or Firm—Mishrilal Jain

[57] ABSTRACT

A modification of the polymerase chain reaction (PCR) technique is described. The method allows the amplification of regions of DNA flanking a single region of known sequence, in contrast to standard PCR which requires two regions of known sequence at opposite ends of the fragment to be amplified. Various advantages of the new method are described.

16 Claims, 4 Drawing Sheets

CUT WITH Sau3A
CIRCULARIZE

II

CUT WITH PstI

III

CIRCULARIZATION OF SINGLE STRANDED DNA FOR PCR

I. CUT WITH HAE III

II. MELT, ANNEAL BRIDGING OLIGO, LIGATE

III. AMPLIFY

FIG. 4

DNA AMPLIFICATION TECHNIQUE

TECHNICAL FIELD

The present invention is generally related to the in vitro technique of DNA amplification, in particular the polymerase chain reaction (PCR). Specifically, the present invention is a method which allows, for the first time, in vitro amplification of DNA adjacent to a single region of known sequence.

BACKGROUND OF THE INVENTION

The PCR technique allows in vitro amplification of DNA which lies between two regions of known sequence. Double stranded target DNA is first melted to separate the DNA strands, and then oligonucleotide (oligo) primers complementary to the ends of the segment which is desired to be amplified are annealed to the template DNA. The oligos serve as primers for the synthesis of new complementary DNA strands, using a DNA polymerase enzyme and a process known as primer extension. The orientation of the primers with respect to one another is such that the 5' to 3' extension product from each primer contains, when extended far enough, the sequence which is complementary to the other oligo. Thus, each newly synthesized DNA strand becomes a template for synthesis of another DNA strand beginning with the other oligo as primer. Repeated cycles of melting, annealing of oligo primers, and primer extension lead to a (near) doubling, with each cycle, of DNA strands containing the sequence of the template beginning with the sequence of one oligo and ending with the sequence of the other oligo. The key requirement for this exponential increase of template DNA is oligo primers complementary to the ends of the sequence desired to be amplified, and oriented such that their 3' extension products proceed toward each other. If the sequence at both ends of the segment to be amplified is not known, complementary oligos cannot be made and standard PCR cannot be performed. The object of the present invention is to overcome the need for sequence information at both ends of the segment to be amplified, i.e. to provide a method which allows PCR to be performed when sequence is known for only a single region, and it is desired to amplify a segment of DNA extending outward in either or both directions from this single region of known sequence.

SUMMARY OF THE INVENTION

The essence of the invention is that by circularizing a restriction enzyme fragment containing the region of known sequence plus flanking DNA, PCR can be performed using oligos whose sequence is taken from the single region of known sequence, and oriented with respect to one another such that their 5' to 3' extension products proceed toward each other by going "around the circle" through what originally was flanking DNA. This leads to amplification of DNA strands containing what was originally flanking DNA. Since the present invention leads to amplification of DNA which lies "outside" of the oligos in the original configuration of the DNA, the method of the present invention is designated herein as "inside-out" PCR.

An object of the present invention is to provide a technique which utilizes sequence information from a single small region for amplification of DNA lying to either or both sides of the region of the known sequence.

UTILITY OF THE INVENTION

The technique of the present invention is useful in many situations. Examples include, but are not limited to: amplification of DNA flanking the integration site of insertion elements, such as retroviruses, knowing only the sequence of the insertion element (retrovirus); amplification of DNA from control regions lying "upstream" or "downstream" of a transcribed gene, knowing only the sequence of the transcribed region or cDNA; amplification of DNA from the edges of introns, knowing only the sequence of the adjacent exon; amplification of segments of cloned DNA lying just inside the "arms" of a cloning vector, such as lambda phage or yeast artificial chromosomes, knowing only the sequence of the vector "arms"; amplification of chromosomal DNA from the opposite end of a (large) restriction enzyme fragment, as in chromosome "jumping", knowing the sequence at only one end of the fragment. These applications and various other objects and advantages will becomes evident from the following detailed description of the invention.

BRIEF DESCRIPTION OF THE DRAWINGS

These and various other objects, features and many of the attendant advantages of the invention will be better understood upon a reading of the following detailed description when considered in connection with the accompanying drawings wherein:

FIG. 1 is a schematic representation of the strategy for amplifying flanking DNA utilizing the method of circularizing double stranded restriction enzyme fragments. I. Shaded area denotes region of known sequence; cross-hatched area denotes flanking DNA, the sequence of which is unknown and which is desired to be amplified. A and B denote oligo primers complementary to opposite strands of DNA from the region of known sequence; arrows indicate the 5' to 3' orientation of the oligos. II. The DNA is cut with a restriction enzyme which does not cut between the 5' ends of the two oligos, and the restriction enzyme fragments are then circularized. For illustrative purposes, the enzyme Sau3A is shown in the figure, although any suitable enzyme could be used which does not cut between the 5' ends of the oligos and which generates a fragment not too small to circularize or too large to amplify by PCR (vide infra). III. The circularized DNA fragment containing the desired flanking DNA sequence is then linearized by cutting with a restriction enzyme which cuts between the 5' ends of the oligos. For illustrative purposes the enzyme PstI is shown in the figure, but any other suitable enzyme could be used which cuts between the 5' ends of the oligos and nowhere else in the circularized fragment of interest. This linearization step is helpful but not mandatory (vide infra). The circularly permuted fragment is now in the proper configuration for what was originally flanking DNA to be amplified with oligos A and B according to standard PCR.

FIG. 2 is a schematic diagram showing the strategy outlined in FIG. 1 applied to the specific case of amplifying cellular DNA flanking an integrated ecotropic provirus of mice. Wavy line denotes flanking cellular DNA; open boxes denote the long terminal repeat (LTR) sequences which occur at the ends of the provirus; solid line denotes proviral DNA with a portion of the env gene indicated. The sequences of the particular oligo primers used in the experiments demonstrating the feasibility of this application (vide infra) are shown in the lower part of the figure. Numbers above the sequence refer to base position in the LTR (1=first base in the U3 portion of the LTR). For comparison, the sequences of corresponding portions of other endogenous LTRs are shown (MCF 247, NZB xeno, and Fv-4); "." indicates the same base as in oligo A or B.

FIG. 3 shows the results of applying this strategy to amplifying cellular DNA flanking the single endogenous ecotropic provirus of BALB/c mice. Left panel: Photograph of ethidium bromide stained agarose gel in which were electrophoresed the amplification products from BALB/c mouse DNA, Chinese Hamster DNA (CH), and DNA from a somatic cell hybrid made between Chinese Hamster and BALB/c cells, and which contained mouse chromosome 5 as the only mouse chromosome (CH chr 5). "−" and "+" denote that the template DNA was out with Sau3A ("−"), or cut with Sau3A, ligated, and cut with PstI ("+"), prior to performing PCR. Size markers ("M") are phiX DNA cut with HaeIII. The lane marked "oligos alone" shows the PCR products when no template DNA was added. Middle panel: Autoradiograph of alkaline transfer of the gel shown in left panel after hybridization to an oligo probe, the sequence of which was taken from a published report of the sequence of cellular DNA flanking the BALB/c ecotropic provirus (vide infra). Right panel: Autoradiograph of the same membrane after stripping and rehybridization to an oligo probe, the sequence of which was taken from a published report of the sequence of ecotropic viruses just upstream of the 3' LTR. (vide infra).

FIG. 4 is a schematic diagram of an alternate strategy for amplifying flanking DNA by circularizing single stranded DNA. For illustrative purposes, the method is shown applied to the amplification of cellular DNA flanking an endogenous ecotropic provirus of mice. I. Genomic DNA is cut with HaeIII, which cuts the sequence GGCC. This generates a "junction" fragment which begins with the HaeIII site in flanking cellular DNA closest to the 5' LTR. The sequence at the proviral end of this fragment is shown. II. The double stranded DNA is melted and an oligo having the sequence of the last 16 bases of the junction fragment, plus the two additional bases CC at its 3' end, is used to anneal to, and circularize, the complementary strand of the "junction" fragment. This circularized fragment is then ligated. III. PCR is then performed using the "circularizing" oligo and another oligo with the opposite orientation from further "upstream" in the proviral LTR.

DETAILED DESCRIPTION OF THE INVENTION

The above and various other objects and advantages of the present invention are achieved by a method of amplification of DNA extending to one or both sides of a single region whose sequence is known, comprising the sequential steps of:
(a) cutting DNA into fragments with a restriction enzyme;
(b) inactivating the restriction enzyme;
(c) circularizing the fragments obtained in step (a) with a DNA ligase;
(d) inactivating the ligase;
(e) recutting the circularized DNA with a different enzyme, which circularly permutes the original DNA fragment; and then
(f) performing polymerase chain reaction (PCR) with oligonucleotide primers whose sequence is taken from a single region of an original, unpermuted DNA, the oligos after circular permutation being complementary to opposite ends of the DNA fragment and in the correct orientation for standard PCR amplification of the circularly permuted DNA.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art.

Unless mentioned otherwise, all chemicals, reagents and the like were of analytical grade and obtained from commercial sources. The following material and methods were preferred.

Restriction enzymes, T4 DNA ligase, T4 DNA polymerase, and T4 polynucleotide kinase were purchased from Bethesda Research Laboratories. Taq polymerase was purchased from Cetus-Perkin Elmer. Agarose was purchased from FMC Corporation. BALB/c mouse DNA, Chinese Hamster DNA, and DNA from the Chinese Hamster-mouse chromosome 5 somatic cell hybrid was a gift from Dr. Christine Kozak, NIH, Bethesda, MD 20892. PCR was performed using a Cetus-Perkin Elmer Thermocycler. Electrophoresis was performed in 45 mM Tris, 45 mM boric acid, 2 mM $Na_2EDTA$. Transfer to Hybond nylon membranes (purchased from Amersham) was done in 0.25M NaOH, 1.5M NaCl, and stripping was done in 0.4M NaOH, according to the manufacturer's suggestions. Oligonucleotides were synthesized on an Applied Biosystems 380B synthesizer, deblocked with $NH_4OH$, and purified by ethanol precipitation. Oligonucleotide probes were end-labelled with $^{32}P$-gamma ATP and T4 polynucleotide kinase as described by Maniatis et al, *Molecular Cloning: A Laboratory Manual*, Cold Spring Harbor Laboratory, 1982, pp 123–126. Hybridization to nylon membranes was performed at room temperature in about 10 ml of hybridization solution consisting of 6× SSC (1× SSC=150 mM NaCl, 15 mM NaCitrate), 5× Denhardt's solution (50× Denhardt's solution=1% Ficoll, 1% polyvinylpyrrolidone, 1% bovine serum albumen), 100 microgram/ml salmon sperm DNA, about $10^7$ dmp of end-labelled oligo probe, and 0.1% sodium dodecyl sulfate (SDS). After hybridization for about 6 to 20 hours, the membranes were washed at room temperature in 6× SSC, 0.1% SDS.

For illustrative purposes, two methods for performing "inside-out" PCR are described, the first involving circularization of double stranded DNA, the second involving circularization of single stranded DNA.

METHOD I

Circularization of double stranded DNA

In this method double stranded DNA is first cut with a restriction enzyme to generate, among other fragments, a "junction" fragment containing a portion of the region of known sequence plus flanking DNA. The double stranded fragments are then circularized with T4 DNA ligase, and PCR is performed with oligos from the region of known sequence. Before performing PCR, it may be helpful, in certain situations, to linearize the circular double stranded DNA template by cutting with a different restriction enzyme which cuts only between the 5' ends of the amplifying oligos. The following are some of the criteria which apply to the starting DNA, the oligos, the choice of restriction enzymes, and the like.

(1) The quantity of DNA needed depends, in general, on its complexity. For example, in case of mammalian DNAs, we use about 1 microgram while for plasmids, 1 nanogram was more than sufficient.

Figure 1:
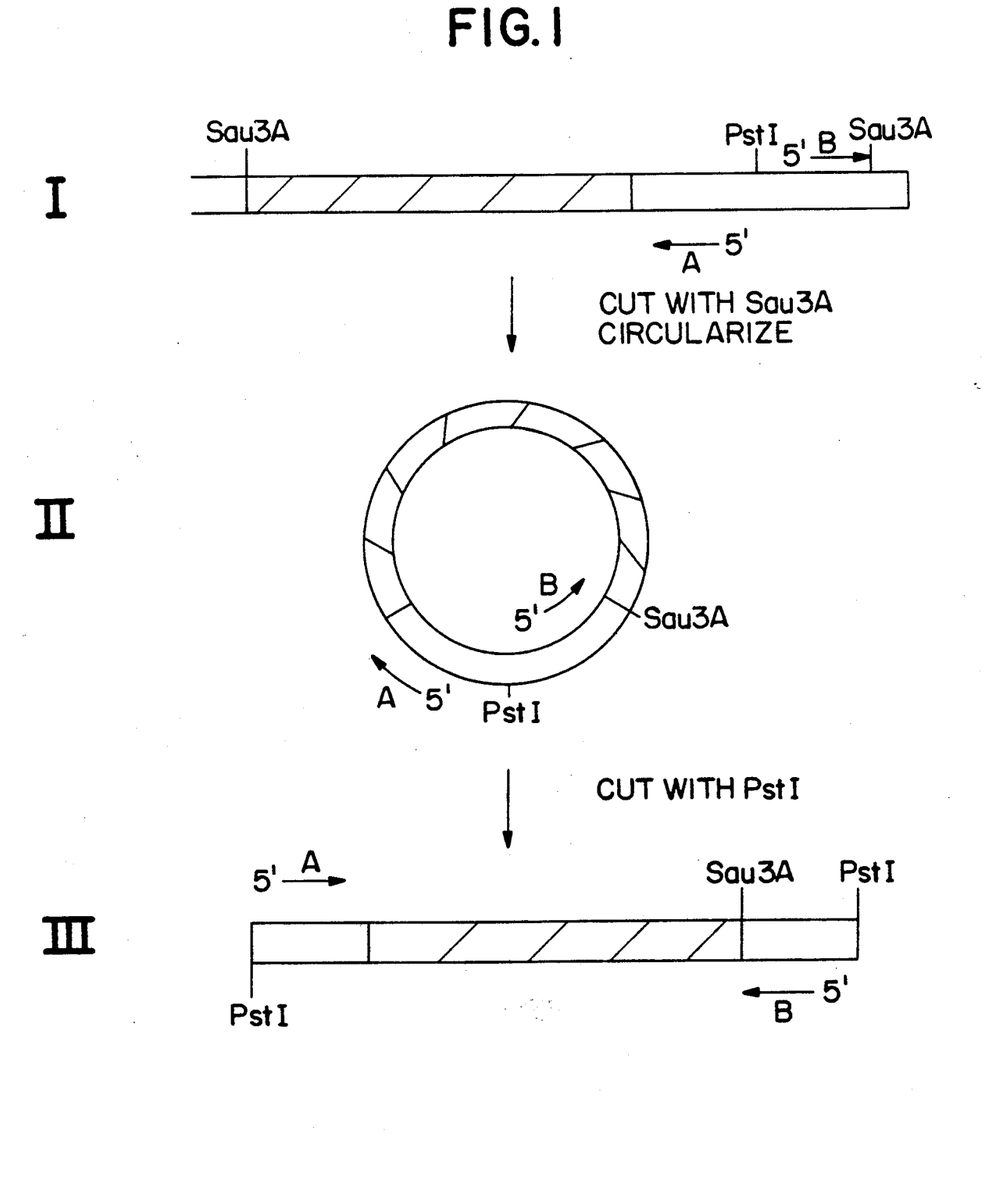

(2) The sequence of the oligos are taken from opposite strands of DNA in the region of known sequence, and are oriented such that their 5' ends are closest to one another (see FIG. 1). Thus, the 5' to 3' extension product from each oligo proceeds "away" from the sequence of the other oligo in the original configuration of the double stranded DNA. It is to be noted that this orientation is opposite to the normal orientation of oligo primers in standard PCR. The 5' ends of the oligos may be modified by the addition of restriction enzyme recognition sequences to facilitate subsequent cloning.

(3) The restriction enzyme used to generate "junction" fragments should be chosen so that the "junction" fragments are longer than about 200 base pairs and shorter than about 2000 base pairs. These restrictions are determined by the facts that it is difficult to circularize double stranded fragments shorter than about 200 base pairs, and difficult to amplify, using PCR, fragments longer than a few kilobases. The upper limit on length may, of course, increase as PCR methodology allows for the amplification of longer fragments. If the sizes of "junction" restriction fragments can be determined in advance, these conditions are usually easily met. If the sizes of such "junction" fragments cannot be determined in advance, then it is reasonable to choose a restriction enzyme which has a four base recognition sequence in order to avoid excessively long fragments. The lower limit on "junction" fragment size will be exceeded if the restriction enzyme chosen does not cut in the region of known sequence for at least 200 bases from the end of the flanking DNA. The restriction enzyme chosen must, of course, generate a "junction" fragment which contains the sequences of both of the amplifying oligos; this requirement is met by choosing the oligos to fit the restriction enzyme instead of vice versa. In order to facilitate circularization of the "junction" fragments, it is desirable to use a restriction enzyme which generates cohesive ends. Sau3A, NlaIII and HhaI are some of the enzymes which generate such cohesive ends and have been successfully used in this procedure. Enzymes which generate "blunt" ends may also be applicable. After cutting, the restriction enzyme is inactivated by standard procedures, such as by heating (if it is heat sensitive), or by phenol extraction followed by chloroform extraction and ethanol precipitation.

(4) The double stranded DNA fragments are then circularized by ligating with T4 DNA ligase. To favor the formation of circles over concatamers, one may ligate the DNA as a dilute solution. The ratio of circles to concatamers can be estimated from the expression (See Maniatis supra pp 286–288)

$$\frac{\text{circles}}{\text{concatamers}} = \frac{1871 \times \text{vol (ml)}}{(\text{length in bp})^{\frac{1}{2}} \times \text{wt (microgram)}}$$

Typically, DNA concentrations of 1 to 10 microgram/ml were used during ligation, which for fragments of about 400 base pairs give ratios of about 100:1 to 10:1. Although ligation is traditionally performed in a buffer which contains up to 1 mM ATP, it was found that ligation could also be performed in the same buffer used for PCR (vide infra) without adding ATP. The occurrence of ligation under these conditions is probably due to the use of relatively large amounts of T4 DNA ligase (about 10 units/50 microliter reaction). (See Weiss et al 1968, J. Biol. Chem., 243: 4556-4563). Alternatively, ligation was performed in PCR buffer to which ATP was added to a final concentration of 66 micromolar. The presence of this amount of ATP did not appear to interfere with subsequent PCR amplification. After ligation, the T4 DNA ligase was inactivated by heating, or by phenol extraction followed by chloroform extraction and ethanol precipitation.

(5) In most of the experiments with mammalian DNA, the double stranded, circularized "junction" fragments were linearized before performing PCR, using a restriction enzyme which cut between the 5' ends of sequences of the amplifying oligos, but which did not cut elsewhere in the "junction" fragment. This linearization step is not absolutely necessary, since "inside-out" PCR was successfully performed on mammalian DNA without this step. Nevertheless, linearization seems to be advantageous since control experiments with circular plasmids showed that linearization permitted amplification starting with 100-fold less template DNA. A possible explanation for the effect of linearization is that rapid ("snap back") reannealing of closed circular template DNA interferes with primer extension. Finding a restriction enzyme which cuts between the 5' ends of the amplifying oligos and nowhere else in the "junction" fragment may, however, be difficult, particularly if restriction sites in the flank are not easily determined. We used restriction enzymes which have 6 base recognition sequences for linearization, in combination with "junction" fragments generated by restriction enzymes with 4 base recognition sequences. In this situation, it is statistically unlikely that the 6 base enzyme will cut elsewhere in the "junction" fragment. Another approach to preventing "snapback" annealing is to "nick" one strand of the double stranded circular "junction" fragment using, for example, heat or digestion with dilute DNAse I in the presence of ethidium bromide. Another alternative procedure which obviates the need for the linearization step is described in Method II (vide infra).

(6) PCR is then performed on the (linearized) "junction" fragments, using the amplifying oligos selected as described in step (2) above, and employing standard PCR techniques (Faloona et al, 1987, Methods in Enzymology, 155: 335-350).

Figure 2:
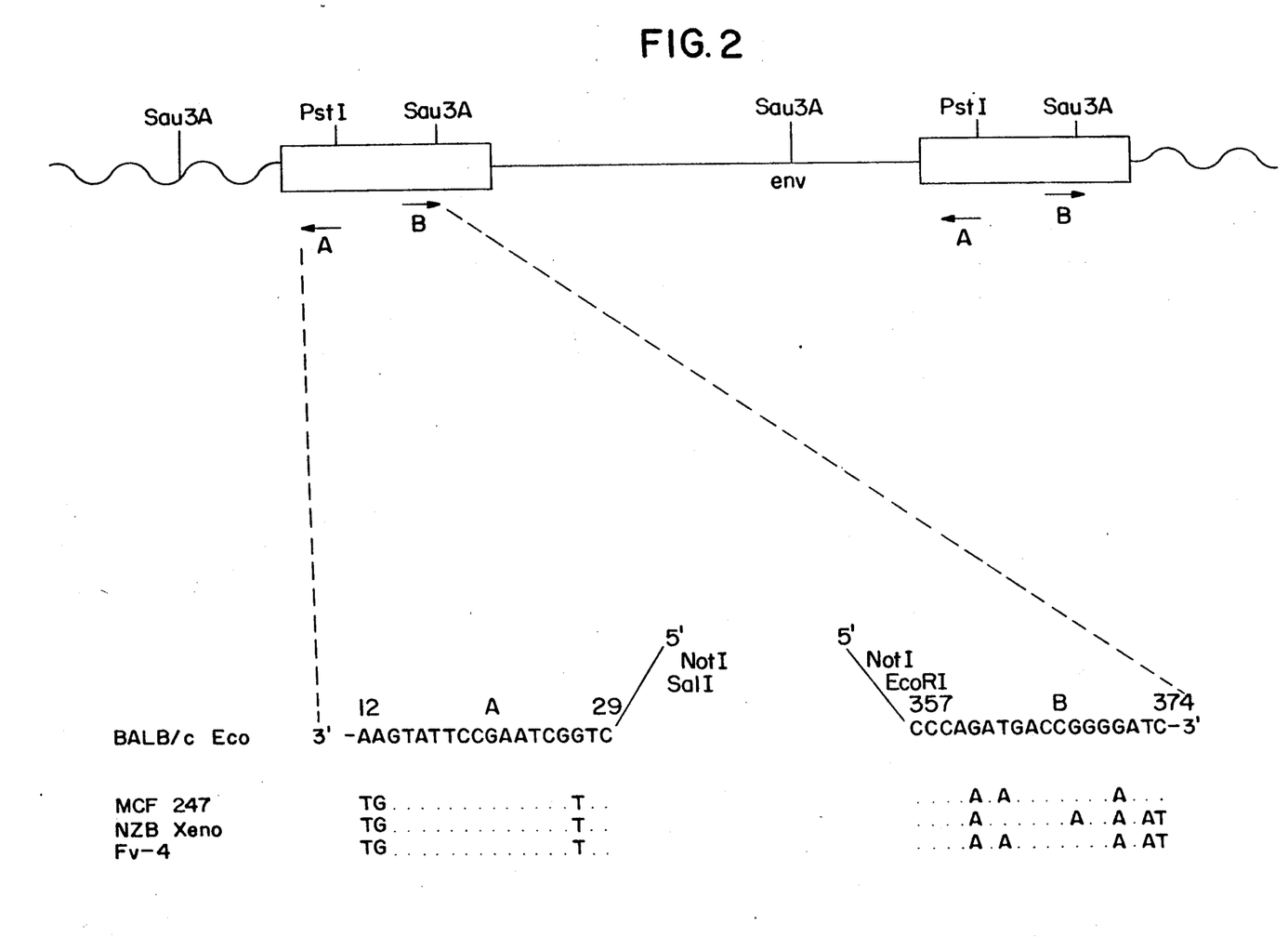
Figure 3:
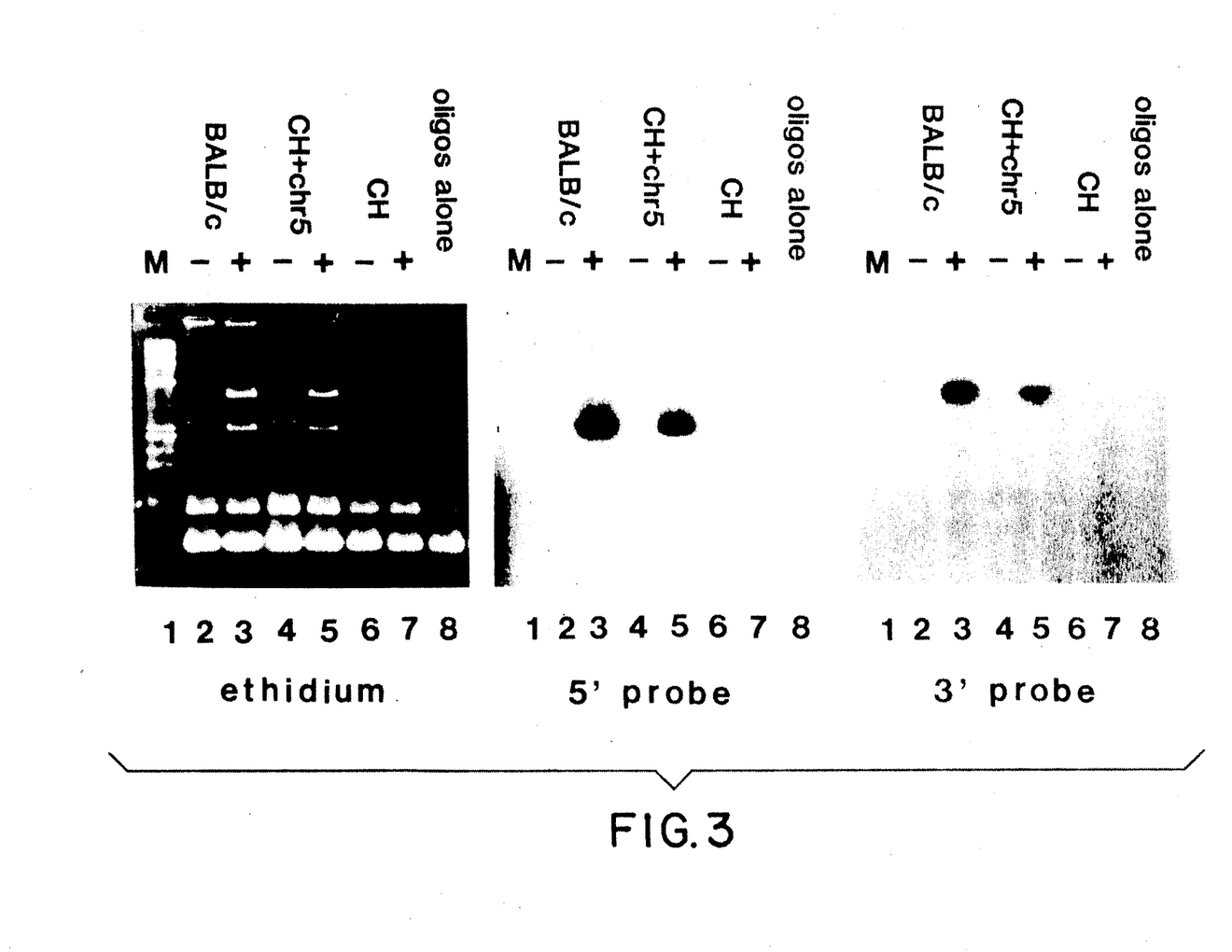

To test Method I of "inside-out" PCR, cellular DNA flanking inherited proviruses in mice was amplified. In particular, cellular DNA flanking inherited ecotropic proviruses was selected for amplification because there are only a few such proviruses in most mouse strains, and some of these sequences have been cloned and sequenced by standard methods, thereby allowing verification of the method of "inside-out" PCR. The oligos used for this test are shown in FIG. 2. Oligos were chosen whose sequences came from the long terminal repeat (LTR) of the provirus; the LTR lies adjacent to cellular DNA at either end of the integrated provirus. While there are only a few ecotropic proviruses per mouse strain, there are many long terminal repeats, the sequences of which may be closely related. In an attempt to amplify only DNA flanking ecotropic LTRs, oligos were chosen from regions of the ecotropic LTR which are known to be highly polymorphic between retroviruses (FIG. 2B). The oligos used were from sequences lying to the "left" of the first Sau3A site in the ecotropic LTR, which begins at base 374. In some cases the sequences of restriction enzyme sites NotI and EcoRI or SalI were appended to the 5' ends of the oligos to facilitate cloning of amplified DNA. The sequences of the amplifying oligos were separated by a PstI site in proviral DNA so that circularized "junction" Sau3A fragments could be linearized with PstI prior to performing PCR. As shown in FIG. 2B, this strategy is expected to lead to amplification of two "junction" fragments from each provirus, one from the 5' LTR and one from the 3' LTR. The fragment arising from the 3' LTR has an expected size of 476 base pairs, based on the generally conserved positions of Sau3A sites in ecotropic proviruses, and the position and size of the amplifying oligos. The size of the fragment arising from the 5' LTR is, in general, unknown, and depends on the position of the Sau3A site in cellular DNA nearest to the 5' LTR. BALB/c mouse DNA was used because this inbred mouse strain contains only one ecotropic provirus, and this provirus is known to be located on mouse chromosome 5. Furthermore, the BALB/c provirus has been cloned along with flanking cellular DNA. Controls included Chinese Hamster DNA (which does not contain any ecotropic proviruses), and DNA from a Chinese Hamster-BALB/c mouse somatic cell hybrid which contains only one mouse chromosome - chromosome 5. One half microgram of each DNA was cut with 10 units of Sau3A in 50 microliters of PCR buffer (10 mM Tris-HCl (pH 8.3), 50 mM KCl, 2 mM MgCl$_2$, and 0.01% gelatin). The Sau3A was inactivated by heating to 65° C. for 15 minutes, and the fragments were circularized by adding 10 units of T4 DNA ligase and incubating at room temperature (about 22°-25° C.) for one hour. Ten units of PstI were then added and the mixture incubated at 37° C. for one hour. Control samples (marked "—" in FIG. 2B) were treated identically except that the steps of ligation and recutting with PstI were omitted. For PCR, 100 picomoles of each oligo, 20 nanomoles each of dATP, dCTP, dGTP AND dTTP, and 2.5 units of Taq polymerase were added along with salts to make the reaction 1× in PCR buffer in a volume of 100 microliters; 100 microliters of mineral oil was then layered on top to prevent evaporation. The tubes were then cycled through 94° C. for 1 minute 30 seconds to melt the DNA, 50° C. for 1 minute 30 seconds to anneal the oligos, and 72° C. for 3 minutes to extend the primers, for 60 cycles, using a Cetus-Perkin Elmer thermocycler. In other experiments, only 30 cycles of PCR were performed with similar results. Ten microliters of the PCR reactions were analyzed by electrophoresis on a composite 1% ME agarose-3% NuSeive agarose gel (FMC Corporation). The gel was stained with 1 microgram/ml ethidium bromide and photographed under UV light. As shown in FIG. 3A, a series of non-specific fragments were seen in the lane marked "oligos alone" (in which PCR was performed in the absence of template DNA), and in the lanes marked "—" (in which genomic DNA was cut with Sau3A, but not subsequently circularized or cut with PstI). In addition, two specific fragments were seen when BALB/c DNA and the Chinese Hamster-mouse chromosome 5 containing DNA were circularized and cut with PstI (lanes marked "+"). The larger of these fragments was of the predicted size to have arisen from the 3' LTR. To confirm the identity of these specific fragments, the gel shown in FIG. 3A underwent capillary transfer to Hy-BOND nylon membrane (Amersham). The membrane was hybridized to an end-labelled oligo, the sequence of which (5'-TGTCTTCATTGGGTACGCGG) was taken from the published sequence for cellular DNA flanking the BALB/c ecotropic provirus on the 5' side (nucleotides 548 to 567 from J. Horowitz, et al. 1987, J. Virol. 61: 701-707). As shown in FIG. 3B, the lower of the two specific fragments hybridized to this probe. The membrane was then stripped and rehybridized to an end-labelled oligo probe, the sequence of which (5'-AATAAAAGATTTTATT) was taken from the published sequence of the region just upstream of the ecotropic virus 3' LTR (nucleotides 7788 to 7803 from W. Herr. 1984, J. Virol. 49: 471-478). As predicted, the larger of the two specific fragments hybridized to this probe. Finally, the presumed 5' "junction" fragment was gel purified, subcloned into plasmid pUC19, and sequenced using the dideoxy technique. The sequence of this fragment was the same as that reported for the sequence flanking the BALB/c ecotropic provirus (nucleotides 492 to 619 from J. Horowitz, supra) with three exceptions: a T inserted after position 525, a G inserted before position 548, and the deletion of an A at position 555. These discrepancies could result from sequence polymorphisms in different substrains of BALB/c mice, polymerase errors during amplification, or sequencing mistakes. These minor discrepancies not withstanding, the results confirm that the "inside-out" PCR technique led to the amplification of the correct "junction" fragments from BALB/c mouse DNA.

METHOD II

Circularization of single stranded DNA

As noted above, Method I has certain limitations, including the need to find a restriction enzyme which generates "junction" fragments not too short to circularize, and another restriction enzyme which cuts between the 5' ends of the sequence of the oligo primers, but not elsewhere in the "junction fragment. Both of these limitations can be eliminated by a method which circularizes single stranded DNA template molecules. Single strands are more flexible than double strands, hence not subject to the >200 base size restriction. Further, since there is no second strand of DNA to "snap back" and interfere with primer extension, there is no need to cut with the "linearizing" enzyme.

Figure 4:
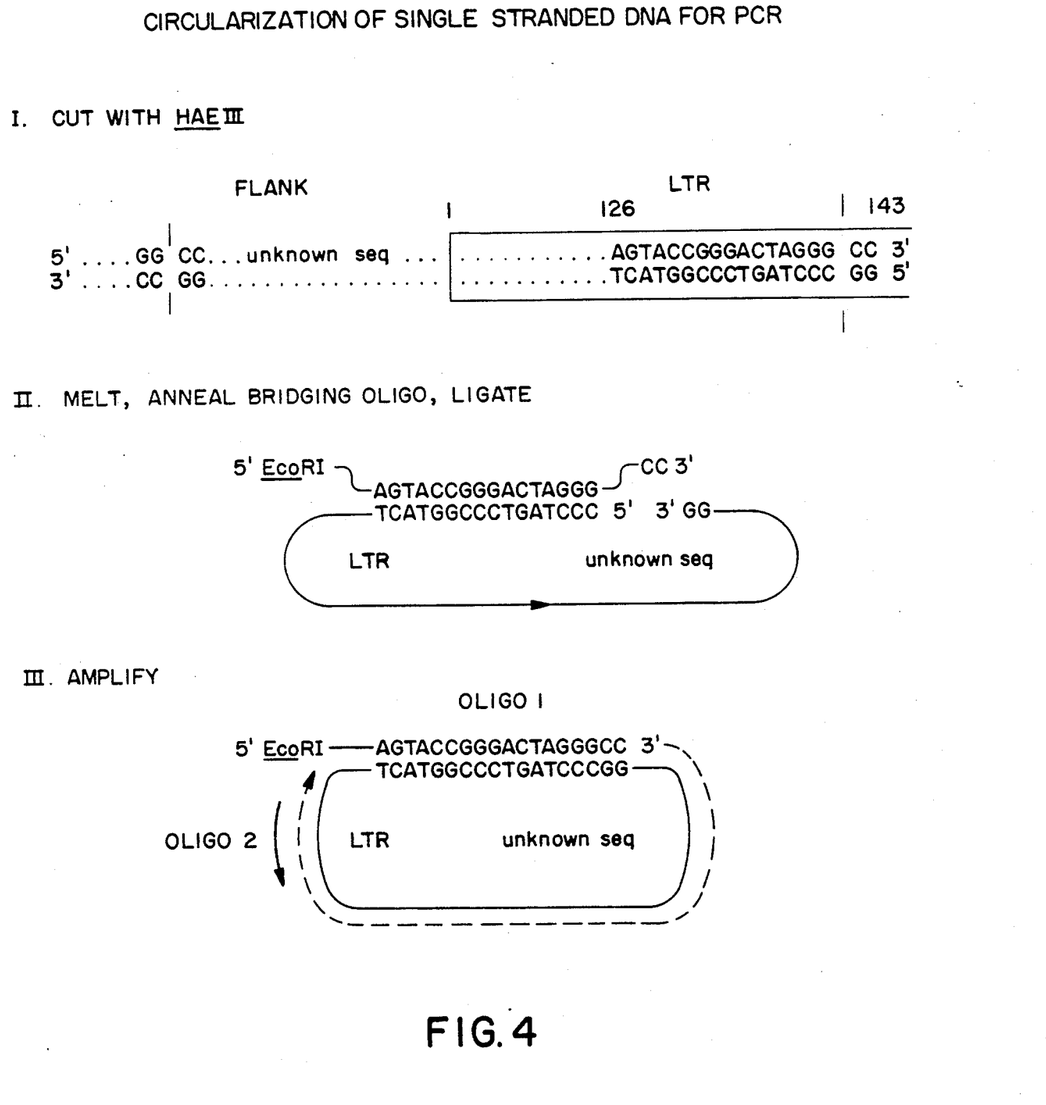

Circularization of single strands can be accomplished by annealing a complementary oligo which overlaps the two ends of the single strand, thereby bringing the two ends together (FIG. 4). In the case of "inside-out" PCR, one can choose a restriction enzyme which cuts in the region of known sequence, and again in the flanking DNA. The sequence of one end of such a fragment is, therefore, known completely, while the sequence at the other end is known to the extent that it terminates with a few bases of the given restriction enzyme recognition sequence. With enzymes that generate 5' overhangs, the number of bases of known sequence at the 3' end of a restriction fragment can be increased by "filling in" the 3' end with T4 DNA polymerase. Thus, one can design a complementary oligonucleotide which will provide at least a two base overlap to circularize one strand of a "junction" fragment terminating in the region of known sequence. This strategy is illustrated in FIG. 4 for the case of a HaeIII fragment terminating in the LTR of an ecotropic provirus. After circularization, the same "circularizing" oligo can be used for primer extension to make a complementary DNA strand which contains a copy of flanking DNA sandwiched between the priming oligo at the 5' end and a portion of the region of known sequence at the 3' end (FIG. 4B). This newly synthesized strand can, in turn, be copied using a second oligo from further "upstream" in the region of known sequence (FIG. 4C). PCR is performed using these two oligos and it can be started right after circularization of the single strand.

The method illustrated in FIG. 4 was applied to plasmid clones of ecotropic proviruses, and shown to be more sensitive than the method of circularization of double strands, in that amplification products of the predicted size could be detected by ethidium bromide staining after 30 cycles of PCR, starting with as little as 100 femtograms of plasmid DNA, whereas about 10 picograms of plasmid DNA were needed using the double strand circularization method. In addition, the single strand circularization method was applied to genomic DNA, and shown to amplify predicted size "junction" fragments from mice carrying endogenous ecotropic proviruses.

It is clear from the foregoing that the technique of the present invention can be used to amplify cellular DNA flanking integrated proviruses, using oligos derived from the provirus sequence only. While standard cloning techniques could be used to obtain the same results, the "inside-out" PCR method is substantially superior, yielding purified "junction" fragment DNA in a single day, compared to a few weeks for standard cloning. Moreover, specific amplified fragments can be used directly for sequencing, or radiolabelled for hybridization probes. This technique, therefore, markedly accelerates and facilitates the analysis of proviral integration sites, which are important, for example, in the search for common proviral integration sites in tumors, a harbinger of cellular oncogenes. The remarkable specificity of PCR allows, in the application described above, amplification of cellular DNA flanking ecotropic LTRs, in mouse DNA containing hundreds of closely related LTRs. This degree of specificity would be difficult to achieve with conventional cloning techniques and oligonucleotide probes. Furthermore, the technique of the present invention can also be used to amplify sequences which, for unknown reasons, are difficult to clone in E. Coli.

In addition, the "inside-out" PCR technique of the present invention can be used in various other situations when it is desired to amplify a segment of DNA lying adjacent to a single region of known sequence. For example, the sequence of transcribed regions of DNA are frequently known through cloning and sequencing of cDNAs. It is often of interest to obtain genomic DNA from regions adjacent to the transcribed sequences: for instance, regulatory regions lying "upstream" or "downstream" of transcribed regions, or intron boundaries, the sequence of which would permit the construction of oligo primers to amplify particular exons. The latter application, amplification of specific exons, provides a way to rapidly search for mutations in patients in whom a specific gene defect is suspected, but from whom it is difficult to obtain mRNA for cDNA cloning. Additionally, the method of "inside-out" PCR could be used to facilitate chromosome "walking" and "jumping", procedures important in the long range mapping of genomic DNAs. Chromosome "walking" refers to the process of obtaining clones of DNA sequences which lie adjacent to a given sequence. This may be important in identifying (and thereby linearly ordering) cloned DNA segments coming from contiguous regions of genomic DNA. "Inside-out" PCR provides another way of chromosome "walking", i.e., obtaining "junction" fragments spanning contiguous segments of genomic DNA.

Chromosome "jumping" refers to the process of obtaining clones of DNA from one end of a large restriction enzyme fragment, given information about the DNA at the other end. In chromosome "jumping", one first circularizes large restriction enzyme fragments, and then attempts to clone "junction" fragments spanning the restriction site about which the fragment was circularized. "Inside-out" PCR provides another way of amplifying the same "junction" fragments, given sequence information (and hence the ability to synthesize oligos) from one end of such a restriction fragment.

In summary, the "inside-out" technique of the present invention, for the first time, provides a simple, efficient and rapid method of DNA amplification in a manner which was not heretofore possible.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method of amplifying double-stranded DNA sequences extending to one or both sides of a single region of known sequence, comprising the steps of:
   (a) cutting double-stranded DNA into fragments with a least one restriction enzyme, wherein at least one restriction fragment comprises a region of known sequence and a flanking DNA sequence to be amplified;
   (b) circularizing said at least one fragment obtained in step (a) with a DNA ligase;
   (c) hybridizing said circularized fragment with two oligonucleotide primers complementary to opposite strands of said region of known sequence, wherein said primers are oriented with their 5' ends toward one another; and
   (d) performing a polymerase chain reaction, wherein 5' to 3' primer extension proceeds from each oligonucleotide primer around the circularized fragment.

2. The method of claim 1, wherein said at least one restriction enzyme generates junction fragments with cohesive ends.

3. The method of claim 2, wherein said restriction enzyme is selected from the group consisting of Sau3A, NlaIII, and HhaI.

4. The method of claim 1, further comprising inactivating the restriction enzyme prior to step (b).

5. The method of claim 1, further comprising inactivating the ligase after step (b).

6. The method of claim 1, further comprising linearizing said circularized fragment prior to step (d) by adding a restriction enzyme reactive only in the region of known sequence, wherein said restriction enzyme cuts between regions corresponding to the 5' ends of said two oligonucleotide primers.

7. The method of claim 1 further comprising nicking one strand of said circularized DNA prior to step (d).

8. The method of claim 7, wherein said nicking is performed by heating or digesting with DNAse I in the presence of ethidium bromide.

9. The method of claim 1, wherein said region of known sequence is an insertion element and said flanking DNA sequence to be amplified is an integration site for said insertion element and flanking regions thereof.

10. The method of claim 9, wherein said insertion element is a proviral insertion element.

11. The method of claim 10, wherein said proviral insertion element is a retroviral insertion element.

12. The method of claim 1, wherein said region of known sequence is a region of a transcribed gene or cDNA thereof and said flanking DNA sequence to be amplified is from control regions upstream or downstream from said known sequence.

13. The method of claim 1, wherein said region of known sequence is an exon or partial sequence thereof and said flanking DNA sequence to be amplified is an adjacent intron.

14. The method of claim 1, wherein said region of known sequence is an intron boundary and said flanking DNA sequence to be amplified is an adjacent exon.

15. The method of claim 14, wherein said exon is from a patient suspected of containing a mutation or genetic defect.

16. A method of amplifying DNA sequences extending to one side of a single region of known sequence comprising the steps of:

(a) generating a double-stranded DNA fragment with a restriction enzyme, wherein said restriction enzyme cuts in a region of known sequence and in flanking DNA extending to one side of said known sequence;

(b) melting the DNA fragment generated in step (a) to produce single-stranded fragments;

(c) contacting a selected single-stranded fragment from step (b) with an oligonucleotide, said oligonucleotide having portions complementary to the 5' and 3' ends of said single-stranded fragment, wherein a first portion of said oligonucleotide is complementary to said region of known sequence located at the 5' or 3' end of said fragment and a second portion of said oligonucleotide is complementary to at least a portion of said flanking DNA located at an end of said single-stranded fragment opposite said region of known sequence;

(d) ligating the 5' and 3' ends of said single-stranded fragment brought into juxtaposition by hybridization to said oligonucleotide to form a circularized single-stranded DNA template;

(e) generating a DNA strand complementary to said circularized template of step (d) through 5' to 3' extension of a first oligonucleotide primer corresponding to a first portion of said region of known sequence; and (f) performing a polymerase chain reaction using said oligonucleotide primer of step (e) and a second oligonucleotide primer corresponding to a second portion of said region of known sequence, wherein said second oligonucleotide primer is complementary to said strand generated in step (e), and primer extension proceeds from each oligonucleotide primer through said flanking DNA to the other oligonucleotide primer.

* * * * *